United States Patent [19]

Berg et al.

[11] Patent Number: 4,718,989

[45] Date of Patent: Jan. 12, 1988

[54] SEPARATION OF ISOPROPANOL FROM ISOPROPYL ACETATE BY EXTRACTIVE DISTILLATION

[76] Inventors: Lloyd Berg; Mark G. Vosburgh, both of 1314 S. Third Ave., Bozeman, Mont. 59715

[21] Appl. No.: 19,423

[22] Filed: Feb. 26, 1987

Related U.S. Application Data

[63] Continuation-in-part of Ser. No. 782,042, Sep. 30, 1985, Pat. No. 4,675,080.

[51] Int. Cl.$^4$ .......................... B01D 3/40; C07C 29/84
[52] U.S. Cl. ......................................... 203/51; 203/56; 203/57; 203/58; 203/60; 203/64
[58] Field of Search ..................... 203/51, 60, 57, 64, 203/58, 18, 56; 568/913, 916, 918; 560/248

[56] References Cited

U.S. PATENT DOCUMENTS

| | | | |
|---|---|---|---|
| 2,575,285 | 11/1951 | Carlson et al. | 203/63 |
| 2,678,905 | 5/1954 | Dice | 203/60 |
| 3,013,953 | 12/1961 | Frazer | 203/60 |
| 3,284,320 | 11/1966 | Fannin et al. | 203/60 |
| 4,379,028 | 4/1983 | Berg et al. | 203/51 |
| 4,473,444 | 9/1984 | Feldman et al. | 203/77 |

*Primary Examiner*—Wilbur Bascomb

[57] ABSTRACT

Isopropanol cannot be completely removed from isopropanol-isopropyl acetate-water mixtures by distillation because of the presence of the minimum ternary azeotrope. Isopropanol can be readily removed from mixtures containing it, isopropyl acetate and water by using extractive distillation in which the extractive agent is a higher boiling ester of phthalic acid. Typical examples of effective agents are diisooctyl phthalate and methyl benzoate, dibutyl phthalate, methyl benzoate and nitromethane.

1 Claim, No Drawings

SEPARATION OF ISOPROPANOL FROM ISOPROPYL ACETATE BY EXTRACTIVE DISTILLATION

This application is a continuation in part of application Ser. No. 782,042 filed Sept. 30, 1985, now U.S. Pat. No. 4,675,080 and describes the separation of the same compounds with different agents.

FIELD OF THE INVENTION

This invention relates to a method for separating isopropanol from isopropyl acetate using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azetropes with them. Usually the extractive agent is introduced a few plates from the top of the column to insure that none of the extractive agent is carried over with the most volatile component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

One of the commercially important ways to manufacture isopropyl acetate is by the catalytic esterfication of isopropanol with acetic acid. Isopropyl acetate (b.p.=88.7° C.), isopropanol (b.p.=82.3° C.) and water (b.p.=100° C.) form a ternary azeotrope boiling at 75.5° C. containing 76 wt. % isopropyl acetate, 13 wt. % isopropanol and 11 wt. % water. isopropyl acetate also forms a binary azeotrope with isopropanol which boils at 80.1° C. and contains 47.4 wt. % isopropyl acetate and a binary azeotrope with water boiling at 75.9° C. containing 88.9 wt. % isopropyl acetate. Isopropanol also forms a binary minimum azeotrope with water which boils at 80.4° C. and contains 87.8 wt. % isopropanol.

Thus in the esterification of isopropanol with acetic acid to form isopropyl acetate and water, the rectification of this mixture has three binary and one ternary azeotrope to content with, and yields the lowest boiling constituent, namely the isopropyl acetate - isopropanol -water ternary azetrope. It is therefore impossible to produce isopropyl acetate from isopropanol and water mixtures by rectification because the lower boiling ternary azeotrope will always come off overhead as the initial product. Any mixture of isopropyl acetate, isopropanol and water subjected to rectification at one atmosphere pressure will produce an overhead product boiling at 75.5° C. and containing 76 wt. % isopropyl acetate, 13 wt. % isopropanol and 11 wt. % water. Extractive distillation would be an attractive method of effecting the separation of isopropyl acetate from isopropanol if agents can be found that (1) will break the isopropyl acetate-isopropanol-water azeotrope and (2) are easy to recover from the isopropyl acetate, that is, form no azeotrope with isopropyl acetate and boil sufficiently above isopropyl acetate to make the separation by rectification possible with only a few theoretical plates.

Extractive distillation typically requires the addition of an equal amount to twice as much extractive agent as the isopropyl acetate-isopropanol-water on each plate of the rectification column. The extractive agent should be heated to about the same temperature as the plate into which it is introduced. Thus extractive distillation imposes an additional heat requirement on the colum as well as somewhat larger plates. However this is less than the increase occasioned by the additional agents required if the separation is to be done by azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is also desirable that the extractive agent be miscible with isopropyl acetate otherwise it will form a two-phase azeotrope with the isopropyl acetate in the receevery column and some other method of separation will have to be employed.

The breaking of this azeotrope by extractive distillation is a new concept. The closest application of the concept might be the breaking of the methyl acetate-methanol azeotrope reported by Yoshida & Oka in Japanese Pat. No. 54/119-411, Sept. 17, 1979, the breaking of the acetone-methanol azeotrope reported by Berg and Yeh, U.S. Pat. No. 4,501,645, Feb. 26, 1985 or the breaking of the butyl acetate-n-butanol-water azeotrope reported by Berg and Yeh, U.S. Pat. No. 4,525,245, June 26, 1985.

OBJECTIVE OF THE INVENTION

The object of this invention is to provide a process or method of extractive distillation that will enhance the relative volatility of isopropanol from isopropyl acetate in their separation in a rectification column. It is a further object of this invention to identify suitable extractive distillation agents which will eliminate the isopropyl acetate-isopropanol-water ternary azeotrope and make possible the production of pure isopropanol and isopropyl acetate by rectification. It is a further object of this invention to identify organic compounds which, in addition to the above constraints, are stable, can be separated from isopropyl acetate by rectification with relatively few theoretical plates and can be recycled to the extractive distillation column and reused with litted decomposition.

SUMMARY OF THE INVENTION

The objects of the invention are provided by a process for separating isopropanol from isopropyl acetate which entails the use of certain oxygenated or nitrogenous organic compounds as the agent in extractive distillation.

DETAILED DESCRIPTION OF THE INVENTION

We have discovered that certain oxygenated or nitrogenous organic compounds, some individually but principally as mixtures, will effectively negate the isopropyl acetate-isopropanol-water ternary azetrope and permit the separation of pure isopropanol from isopropyl acetate by rectification when employed as the agent in extractive distillation. Table 1 lists a number of phthalates and their mixtures and approximate proportions that we have found to be effective. The data in Table 1 was obtained in a vapor-liquid equilibrium still. In each case, the starting material was the isopropyl acetate-isopropanol-water azeotrope. The ratios are parts by weight of extractive agent used per part of isopropyl acetate-ispropanol-water azeotrope. The phthalates that are effective are dimethyl phthalate, diethyl phthalate, dibutyl phthalate, dihexyl phthalate, diisooctyl phthalate, diisononyl phthalate, diisodecyl phthalate, butyl benzyl phthalate and butyl cyclohexyl phthalate.

The relative volatility shown in Table 1 corresponds to the ratio employed. For example, one part of dimethyl phthalate with one part of isopropyl acetate-isopropanol-water azeotrope gives a relative volatility of 1.8. One half part of dimethyl phthalate mixed with one half part of benzyl benzoate with one part of the isopropyl acetate-isopropanol-water azeotrope gives a relative volatility of 2.0.

TABLE 1

Extractive Agents Which Contain Phthalates

| Compounds | Ratios | Relative Volatility |
|---|---|---|
| Dimethyl phthalate | 1 | 1.8 |
| Diethyl phthalate | " | 1.5 |
| Dibutyl phthalate | " | 1.4 |
| Dihexyl phthalate | " | 1.3 |
| Diisooctyl phthalate | " | 1.5 |
| Diisononyl phthalate | " | 2.2 |
| Diisodecyl phthalate | " | 1.3 |
| Butyl benzyl phthalate | " | 1.3 |
| Butyl cyclohexyl phthalate | " | 1.4 |

TABLE 1-continued

Extractive Agents Which Contain Phthalates

| Compounds | Ratios | Relative Volatility |
|---|---|---|
| Dimethyl phthalate, Benzyl benzoate | 1/2:1/2 | 2.0 |
| Dimethyl phthalate, Ethyl benzoate | " | 1.8 |
| Dimethyl phthalate, Methyl benzoate | " | 2.0 |
| Dimethyl phthalate, Glycerol triacetate | " | 1.8 |
| Dimethyl phthalate, Nitroethane | " | 2.1 |
| Diethyl phthalate, Ethyl benzoate | " | 1.4 |
| Diethyl phthalate, Methyl benzoate | " | 2.2 |
| Dibutyl phthalate, Adiponitrile | " | 1.3 |
| Dibutyl phthalate, Ethyl benzoate | " | 1.9 |
| Dibutyl phthalate, Methyl benzoate | " | 2.1 |
| Dibutyl phthalate, Hexylene glycol diacetate | " | 1.3 |
| Dibutyl phthalate, Nitromethane | " | 2.0 |
| Dibutyl phthalate, Nitroethane | " | 2.1 |
| Dibutyl phthalate, 2-Nitropropane | " | 2.1 |
| Dihexyl phthalate, Adiponitrile | " | 1.9 |
| Dihexyl phthalate, Ethyl benzoate | " | 1.4 |
| Dihexyl phthalate, Methyl benzoate | " | 1.8 |
| Dihexyl phthalate, Ethylene glycol diacetate | " | 1.3 |
| Dihexyl phthalate, Hexylene glycol diacetate | " | 1.2 |
| Dihexyl phthalate, Glycerol triacetate | " | 2.1 |
| Dihexyl phthalate, Diethylene glycol diethyl ether | " | 1.3 |
| Dihexyl phthalate, Propylene carbonate | " | 1.5 |
| Diisooctyl phthalate, Adiponitrile | " | 1.6 |
| Diisooctyl phthalate, Ethyl benzoate | " | 1.9 |
| Diisooctyl phthalate, Methyl benzoate | " | 1.5 |
| Diisononyl phthalate, Adiponitrile | " | 1.9 |
| Diisononyl phthalate, Methyl benzoate | " | 2.1 |
| Diisodecyl phthalate, Methyl benzoate | " | 2.1 |
| Butyl benzyl phthalate, Benzyl benzoate | " | 2.0 |
| Butyl benzyl phthalate, Ethyl benzoate | " | 2.1 |
| Butyl benzyl phthalate, Methyl benzoate | " | 2.1 |
| Diethyl phthalate, Methyl benzoate, 1-Nitropropane | 1/3:1/3:1/3 | 2.1 |
| Dibutyl phthalate, Methyl benzoate, 1-Nitropropane | " | 2.1 |
| Dibutyl phthalate, Methyl benzoate, Nitromethane | " | 2.1 |
| Dibutyl phthalate, Methyl benzoate, 2-Nitropropane | " | 2.2 |

TABLE 2

Data From Runs Made In Rectification Column.

| Agent | Time min. | Stillpot Temp. °C. At Start | Stillpot Temp. °C. Sampling | Overhead Temp. When Sampling | Weight % Isopropanol Overhead | Weight % Isopropanol Bottoms | Relative Volatility | |
|---|---|---|---|---|---|---|---|---|
| Methyl benzoate | 60 | 79.2 | 108.2 | 78.2 | 54.9 | 15.1 | 1.53 | |
|  | 90 | 79.2 | 117.2 | 77.0 | 56.5 | 17.5 | 1.49 | |
|  | 120 | 79.2 | 123.2 | 76.6 | 56.9 | 12.4 | 1.64 | |
|  |  |  |  |  |  |  | 1.55 | average |
| Methyl benzoate, Diisooctyl phthalate | 60 | 76.8 | 95.4 | 76.4 | 74.6 | 40.7 | 1.38 | |
|  | 90 | 76.8 | 102.4 | 76.6 | 75.1 | 37.0 | 1.44 | |
|  | 120 | 76.8 | 107.2 | 74.8 | 76.1 | 36.4 | 1.46 | |
|  |  |  |  |  |  |  | 1.43 | average |

| Notes: Agent | Feed, % Isopropanol | Agent Flow ml/min. | Boilup Rate ml/min. | Agent Temp. | Agent Comp. Weight % |
|---|---|---|---|---|---|
| Methyl benzoate | 13 | 20 | 10–20 | 70–75 | 100% MeBenzoate |
| Methyl benzoate, Diisooctyl phthalate | 13 | 20 | 10–20 | 65–75 | 50% MeBenzoate |

Two of the compounds and mixtures listed in Table 1 whose relative volatility had been determined in the vapor-liquid equilibrium still, were then evaluated in a glass perforated plate rectification column possessing 4.5 theoretical plates. The isopropyl acetate-isopropanol-water mixture studied contained 76 wt. % isopropyl acetate, 13 wt. % isopropanol and 11 wt. % water which is the azeotrope composition. In every case, the overhead was richer than 13 wt. % isopropanol and the results are tabulated in Table 2. without the extractive agent, the overhead would be the azeotrope, 13 wt. % isopropanol. This proves that the extractive agent is negating the azeotrope and makes rectification proceed as if the azeotrope no longer exists and brings the more volatile component, isopropanol, out as overhead product. It is out belief that this is the first time that this has been accomplished for this azeotrope.

The data in Table 2 was obtained in the following manner. The charge was 76 wt. % isopropyl acetate, 13 wt. % isopropanol and 11 wt. % water and after a half hour of operation in the 4.5 theoretical plate column to establish equilibrium, methyl benzoate at 70°-75° C. and 20 ml/min. was pumped in. The rectification was continued for two hours with sampling of the overhead and bottoms after one hour, 1.5 hours and two hours. The average of the three analyses was 56.1 wt. % isopropanol in the overhead and 45 wt. % in the bottoms which gives a relative volatility of 1.55. This indicates that the ternary azeotrope has been negated and separation accomplished.

THE USEFULNESS OF THE INVENTION

The usefulness or utility of this invention can be demonstrated by referring to the data presented in Tables 1 and 2. All of the successful extractive distillation agents show that isopropyl acetate, isopropanol and water can be separated from their ternary azeotrope by means of distillation in a rectification column and that the ease of separation as measured by relative volatility is considerable. Without these extractive distillation agents, no improvements above the azeotrope composition will occur in a rectification column. The data also show that the most attractive agents will operate at a boilup rate low enough to make this a useful and efficient method of recovering high purity isopropanol from any mixture of these three including the ternary minimum azeotrope. The stability of the compounds used and the boiling point difference is such that complete recovery is obtainable by a simple distillation and the amount required for make-up is small.

WORKING EXAMPLES

EXAMPLE 1

The isopropyl acetate - isopropanol - water azeotrope is 76 wt. % isopropyl acetate, 13 wt. % isopropanol, 11 wt. % water. Fifty grams of the isopropyl acetate - isopropanol - water azeotrope and fifty grams of diethyl phthalate were charged to an Othmer type glass vapor-liquid equilibrium still and refluxed for eleven hours. Analyses of the vapor and liquid by gas chromatography gave a vapor composition of 21.7% isopropanol, 78.3% isopropyl acetate; a liquid composition of 15% isopropanol, 85% isopropyl acetate. This indicates a relative volatility of 1.5.

EXAMPLE 2

Fifty grams of the isopropyl acetate - isopropanol - water azeotrope, 25 grams of methyl benzoate and 25 grams of diisooctyl phthalate were charged to the vapor-liquid equilibrium still and refluxed for 12 hours. Analyses indicated a vapor composition of 20.2% isopropanol, 79.8% isopropyl acetate; a liquid composition of 15% isopropanol, 85% isopropyl acetate which is a relative volatility of 1.43.

EXAMPLE 3

Fifty gram of the isopropyl acetate - isopropanol - water azeotrope, 17 grams dibutyl phthalate, 17 grams of methyl benzoate and 17 grams of nitromethane were charged to the vapor-liquid equilibrium still and refluxed for 12 hours. Analyses indicated a vapor composition of 21.7% isopropanol, 78.3% isopropyl acetate; a liquid composition of 11.5% isopropanol, 88.5% isopropyl acetate which is a relative volatility of 2.13.

EXAMPLE 4

A solution of 304 grams of isopropyl acetate, 52 grams of isopropanol and 44 grams of water was placed in the stillpot of 4.5 theoretical plate glass perforated plate rectification column. When refluxing began, an extractive agent comprising 50% methyl benzoate and 50% diisooctyl phthalate was fed to the top of the column at a feed rate of 20 ml/min. and a temperature of 65°-75° C. After establishing the feed rate of the extractive agent, the heat input to the isopropyl acetate, isopropanol and water in the stillpot was adjusted to give a total reflux rate of 10-20 ml/min. Having established the reflux rate, the column was allowed to operate for one hour. After one hour of steady operation, overhead and bottoms samples of approximately two ml. were collected and analysed using gas chromatography. The overhead analyses were 74.6% isopropanol, 25.4% isopropyl acetate; the bottoms analyses were 40.7% isopropanol, 59.3% isopropyl acetate. Using these compositions in the Fenske equation with the number of theoretical plates in the column being 4.5, gave an average relative volatility of 1.38 for each theoretical plate. After 1½ hours of total operation, the overhead composition was 75.1° isopropanol, 24.9% isopropyl acetate and the bottoms composition was 37% isopropanol, 63% isopropyl acetate. This gave an average relative volatility of 1.44 for each theoretical plate. After two hours of total operation, the overhead was 76.1% isopropanol, 23.9% isopropyl acetate and the bottoms was 36.4% isopropanol, 63.6% isopropyl acetate. This gave an average relative volatility 1.46 for each theoretical plate.

What is claimed is:

1. A method for recovering isopropanol from a mixture of isopropyl acetate, isopropanol and water which comprises distilling a mixture of isopropyl acetate, isopropanol and water in a rectification column in the presence of about one to two parts of extractive agent per part of isopropyl acetate-isopropanol-water mixture, recovering isopropanol as overhead product and obtaining the extractive agent, isopropyl acetate and water from the stillpot, the extractive agent comprises a phthalate containing from ten to twenty-eight carbon atoms and at least one material from the group consisting of benxyl benzoate, ethyl benzoate, methyl benzoate, glycerol triacetate, nitroethane, nitromethane, 1-nitropropane, 2-nitropropane, ethylene glycol diacetate, hexylene glycol diacetate, adiponitrile, diethylene glycol diethyl ether and propylene carbonate.

* * * * *